US008778418B2

(12) United States Patent
Bisterfeld Von Meer

(10) Patent No.: US 8,778,418 B2
(45) Date of Patent: Jul. 15, 2014

(54) METHOD OF OBTAINING HEMP PLANT JUICE AND USE OF SAME FOR THE PRODUCTION OF BEVERAGES

(75) Inventor: Galathea U. Bisterfeld Von Meer, Hamburg (DE)

(73) Assignees: Claremont Collection Handelsgesellschaft mbH, Hamburg (DE); Galathea Ute Bisterfeld Von Meer, Hamburg (DE)

( * ) Notice: Subject to any disclaimer, the term of this patent is extended or adjusted under 35 U.S.C. 154(b) by 0 days.

(21) Appl. No.: 13/980,304

(22) PCT Filed: Jan. 18, 2012

(86) PCT No.: PCT/EP2012/050730
§ 371 (c)(1),
(2), (4) Date: Nov. 1, 2013

(87) PCT Pub. No.: WO2012/098167
PCT Pub. Date: Jul. 26, 2012

(65) Prior Publication Data
US 2014/0044807 A1    Feb. 13, 2014

(30) Foreign Application Priority Data

Jan. 18, 2011 (DE) .......................... 10 2011 009 074
Jan. 18, 2011 (DE) ..................... 20 2011 001 759 U
Feb. 8, 2011 (DE) .......................... 10 2011 003 819

(51) Int. Cl.
*A01N 65/00* (2009.01)
(52) U.S. Cl.
USPC ........................................................ 424/725
(58) Field of Classification Search
None
See application file for complete search history.

(56) References Cited

U.S. PATENT DOCUMENTS

2008/0305236 A1   12/2008   Tatarliov

FOREIGN PATENT DOCUMENTS

| AT | 002501 U1 | 12/1998 |
| CN | 1116112 A | 2/1996 |
| CN | 1718708 A | 1/2006 |
| CN | 1718709 A | 1/2006 |
| CN | 101785525 A | 7/2010 |
| DE | 4410768 A1 | 10/1994 |
| DE | 69304347 T2 | 2/1997 |
| DE | 19631830 A1 | 2/1998 |
| DE | 19650018 A1 | 6/1998 |
| DE | 202004018692 U1 | 3/2005 |
| DE | 102007032832 A1 | 1/2009 |
| DE | 202011001759 U1 | 4/2011 |
| DE | 102011009074 A1 | 7/2012 |
| EP | 0878536 A2 | 11/1998 |
| ES | 2281287 A1 | 9/2007 |
| KR | 20050026768 A | 3/2005 |
| WO | WO-2009039843 A2 | 4/2009 |

OTHER PUBLICATIONS

Chen, James C.P.: Cane Sugar Handbook, New York : John Wiley & Sons, 1985.—ISBN 0-471-86650-4.
Database Medline [Online] US National Library of Medicine (NLM), Bethesda, MD, US: Apr. 1990. Mahdihassan S: "A brief account of the fractions of soma.", XP002680140. Database accession No. NLM22557699 & Ancient Science of Life Apr. 1990 LNKD—PUBMED:22557699, vol. 9, No. 4, Apr. 1990, pp. 207-208, ISSN: 0257-7941.
Database WPI Week 199741 Thomson Scientific, London, GB: AN 1997-436166 XP002680146, (& CN 1 116 112 A (Shao L) Feb. 7, 1996.
Database WPI Week 200762 Thomson Scientific, London, GB: AN 2007-886906 XP002680139, (& ES 2 261 287 A1 (Cerdeira Campos J) Sep. 16, 2007.
Database WPI Week 201060 Thomson Scientific, London, GB: AN 2010-K61492 XP002680141, (& CN 101 785 525 A (Gao S) Jul. 28, 2010.
International Preliminary Report on Patentability from corresponding International Application No. PCT/EP2012/050730, dated Jan. 25, 2013.
International Search Report from corresponding International Application No. PCT/EP2012/050730, dated Jul. 17, 2012.
Laydeem: "Juicing Raw Cannabis for Greater Health", Berkeley Patients Care Collective, Sep. 18, 2010, pp. 1-2, XP002680138, Retrieved from the internet: URL:http://berkeleypatientscare.com/2010/09/18/juicing-raw-cannabis-for-greater-health/ [retrieved on Jul. 12, 2012].
Pant et al.: "Diversity and indigenous household remedies of the inhabitants surrounding Mornaula reserve forest in West Himalaya", Indian Journal of Traditional Knowledge Resources, New Delhi, New Delhi-India, vol. 8, No. 4, Oct. 1, 2009, pp. 606-610, XP018027576, ISSN: 0972-5938.

(Continued)

*Primary Examiner* — Michael Meller
(74) *Attorney, Agent, or Firm* — Marshall, Gerstein & Borun LLP

(57) ABSTRACT

The present invention relates to a method for producing beverages on the basis of juice from the hemp plant. The invention relates to a method for obtaining juice suitable for human consumption from the hemp plant, wherein the complete hemp stem is pressed after harvest without prior drying or retting. The invention further provides a method for obtaining juice from the hemp plant, wherein the upper leafy part of the hemp plant is cut, the leaves are stripped of the remaining stem, fibers and shives being separated from each other at the stem, the leafy part of the stem, the fibers and the shives being pressed individually under pressure and the so obtained pressed juices are being mixed in a controlled manner. In a yet further aspect, the invention relates to a method for the manufacturing of beverages on the basis of juice from the hemp plant, wherein the hemp juice is mixed with yeast and than fermented.

17 Claims, No Drawings

(56) References Cited

OTHER PUBLICATIONS

Peiretti: "Influence of the growth stage of hemp (*Cannabis sativa* L.) on fatty acid content, chemical composition and gross energy", Agricultural Journal, vol. 4, No. 1, Jan. 1, 2009, pp. 27-31, XP55032565, ISSN: 1816-9155.

Purkayastha et al.: "Biological activities of ethnomedicinal claims of some plant species of Assam", Indian Journal of Traditional Knowledge, Resources, New Delhi, New Delhi-India, vol. 5, No. 2, Apr. 1, 2006, pp. 229-236, XP018021380. ISSN: 0972-5938.

The Cannabia Co: "dupetit/Natural Products. The original legal hemp beer Cannabia", Internet Citation, 1996, XP002124269, Retrieved from the Internet: URL:http://www.dupetit.de/english/hage02.htm [retrieved on Nov. 23, 1999].

METHOD OF OBTAINING HEMP PLANT JUICE AND USE OF SAME FOR THE PRODUCTION OF BEVERAGES

The present invention relates to a method of obtaining juice from the hemp plant, i.e. *Cannabis Sativa* (Cannabaceae) plant, certified by the EU (not usable as a narcotic drug), and a juice produced by the method of the invention which is suitable for human consumption. The present invention further relates to a method for the production of beverages of juice from the hemp plant, which are suitable for human consumption.

BACKGROUND OF THE INVENTION

Hemp, i.e. *Cannabis Sativa* belongs to the family of Cannabicea and is the next relative to hop. It has been cultivated over the centuries on all continents, in all climates and on all types of soils. It is a very undemanding and tolerant plant, but it does not tolerate frost, i.e. it has to be harvested before freezing temperatures set in. The usable parts of the plant are the roots, the fibers, the wood shives, the leaves, the leafy blossom tops and the seeds.

Breeds/species that are applied commercially and that are not used as narcotics are termed "industrial hemp", to which also the present invention refers. Industrial hemp is predominantly cultivated for obtaining hemp fibres, and products like hemp shives, hemp seeds as well as the resulting hemp oil and hemp bloom and leaves. There is an overall of about 41 species certified by the EU that are low in tetra hydro cannabinol (THC) content for cultivation of hemp. In contrast to other species, they contain a very high percentage of fibres of 30-40%. These species all have a very low or no THC (tetrahydrocannabinol) content and cannot be used for producing narcotic drugs.

Leave and bloom of the hemp plant can be turned into essential hemp oils. These water steam distillates are used as taste enhancers in nutrition or aromatic substances for example in detergents. Hemp oil can also be gained from the hemp seeds. Hemp seeds have been an indispensable ingredient for bird food for a long time.

Hemp fibres are separated from the rest of the plant by breaking and milling the stem. Coarse fleece or fine cell material is produced depending on the length of the obtained fibre. Hemp fibres are sought-after as insulating material because of their longevity and resistance to vermin. They are also suitable for the production of textiles and paper. One classical usage is as an impervious material of pipe threads. System mechanics for sanitary, heater and air conditioning technology use hemp fibres to seal water pipes and heater pipes.

The shives are the remains of the woodened parts of the plant that are not suitable for the preparation of fibres. The hemp shives are predominantly used as litter for horses.

The sowing of the hemp in Europe is between the middle of April to the end of July using seed drills to attain a seed depth of 4-6 cm. Harvest of the fibre hemp is achieved with special machines or with harvesting means adapted to the hemp harvest at the time of the main blossom of the male plants and it can extend from the end of July to the end of October or 100 days after sowing, respectively, depending on the species and sowing conditions. Depending on the intended use of the hemp fibre, treatment after harvest on the field can vary. For the processing of the long fibres, the hemp straw will be laid out in a parallel way and dried. The drying is followed by calcination and a renewed drying on the field. To prepare for fibre extraction of the short fibre and total fibre line, the hemp straw on the field is cut and roasted and pressed into round and cuboid bales afterwards. If the seeds are used as well, harvest will be during ripeness of the seeds in the middle of September to the middle of October.

The object of the present invention is to provide diverse additional uses of the valuable hemp i.e. *Cannabis Sativa* (Cannabaceae) plant, especially of hemp certified by the EU (not usable as a narcotic drug) for human consumption and livestock feed, and for the topical application on humans and animals. It has now been found that hemp provides nutritional and medicinal benefits, at the same time preventing its misuse for intoxication (non-narcotic *Cannabis Sativa*).

Hence, a method for the production of juice from the hemp plant is provided. Further, a method for the production of beverages on the basis of such hemp juice is provided.

SUMMARY OF THE INVENTION

According to a first embodiment, the object is achieved by a method for obtaining juice from a hemp plant comprising the steps of harvesting the hemp prior to the seed ripening, and pressing the complete hemp stem without any previous drying or retting.

According to a second embodiment the problem is solved by a method for obtaining juice which is suitable for human consumption from a hemp plant comprising the steps of
  a) harvesting the hemp prior to the seed ripening;
  b) cutting the upper leafy part of the stem;
  c) stripping the leaves from the remaining stem;
  d) separating fibres and shines from each other at the stems;
  e) pressing the leafy part of the stem, the fibres and the shives separately under pressure; and
  f) mixing the so obtained juices.

The hemp juice can be obtained from three different parts of the hemp plant:
  a) the upper leafy third of the hemp stem for a beverage with strong flavour and dark colour;
  b) the fibrous part of the remaining two thirds of the hemp stem for a beverage with a less strong flavour and medium colour, and
  c) the shives for a light beverage with light colour.

The hemp juice as basis for the beverage can also be made of the different parts a) and b), a) and c), b) and c) or a), b) and c) mixed in different proportions.

The present invention further provides a method for the production of beverages on the basis of juices from the hemp plant, wherein the hemp juice is mixed with yeast extract and fermented.

DETAILED DESCRIPTION OF THE INVENTION

The present invention relates to methods for the production of juice from the hemp plant. According to a first embodiment, the hemp plant is pressed immediately after harvesting as whole plant or preferably after separation of the leaves and blooms without a prior drying or retting of the harvested plant.

Preferably, the plant is cleaned from soil and then pressed as described below, preferably using an extruder or, most preferably, press rolls. In particular the juice is cold-pressed from the freshly harvested *Cannabis* plant. The juice thus obtained can be used as a beverage, processed into a carbonated beverage, cosmetic product or fermented to an alcoholic beverage and distilled if necessary.

Preferably the juices are pressed separately from the roots, the fibers, the wood shives and the leaves plus the leafy blossom tops and those juices are mixed in a controlled way for human consumption or application. This is the preferred method to fulfill the given tasks of obtaining and preserving the full natural nutritional and the full natural medicinal benefits from the *Cannabis* plants for human or animal consumption and application.

Alternatively, the upper leafy part of the stem is separated from the remainder of the plant immediately after harvest of the hemp. The upper leafy part make up about $\frac{1}{3}^{th}$ to $\frac{1}{4}^{th}$ of the length of the hemp plant in the upper part. At the lower part of the green and juicy stem, the separation of the fibrous coat of the hemp stem—the "fibres" from the wooden interior of the stem—the "shives" is performed.

For the quality of the beverages and additional products from the hemp juice, the separation of the fibres and shives as well as the separation of the upper, leafy part of the stem prior to pressing is advantageous. The pressed juices of the fibres and shives as well as these from the upper leafy part of the stem have a different taste, smell and colour. The controlled mixture of these fluid proportions of the hemp plant allows for the production of various beverages and products for human consumption.

After secession of the upper leafy part of the hemp stem, the remaining lower part of the hemp plant is preferably cleaned from soil and/or preferably hackled into smaller parts. Preferably, the remaining lower part of the hemp plant is hackled into parts having a length of between 5 and 50 cm, preferably between 10 and 40 cm.

Separation of fibres and shives can be achieved in different ways. The machines already used for the separation of the fibres and shives of the traditionally roasted or dried and stored hemp, respectively, are suitable for the methods of the present invention. The hackling of the remaining lower part of the hemp plant and the subsequent separation of fibres and shives is preferably accomplished using rotating blades. The fibres sticking out of the plant from the previous hackling stick to the rotating blades, while the shives peel off and are thus separated from the fibres.

Prior to pressing, the plants are preferably washed from soil moieties or the soil moieties are removed by compressed air. Preferably, the stems are washed after removal of the leaves.

The pressing of the leafy part of the stem, the fibres and the shives is accomplished individually under pressure. Every usual press, like a wine press can be used. Preferably, the leafy part of the stem, the fibres and/or shives are pressed at a pressure of 3 to 600 bar, preferably 10 to 300 bar, more preferably 30 to 200 bar, preferably with twin-screw extruder (similar to the small commercial "Green Star Juice Extractor") and/or a cylindrical hydraulic press, and/or a water-press, and/or a multiple roller press (smooth and/or rifled), and/or a modern wine press. The pressing of the whole hemp plant, optionally exempt from leaves and/or blooms according to the first embodiment, is preferably carried out in an extruder or a press roll, preferably at a pressure of 3 to 600 bar, preferably 10 to 300 bar, more preferably 20 to 200 bar. Preferred for these parts of the plant with delicate fibers are the twin-screw extruders that cut the fibers to pieces of about 1 to 2 cm depending on the winding of the screws and then press with high pressure through a sieve. The contact with oxygen in the roller press and the water-press darkens the color of the juice from green to brown. Therefore to produce juices of green color for direct human consumption or application those presses that protect the *Cannabis* juice from oxygen are preferred.

The type of pressing will also depend on the further intended processing of the residue. For example, if the fibres are turned into textiles or the shines into paper or cell material, an extruder is preferred as a high pressure can be applied. A high pressure can extract precious oily proportions from the hemp. For the further processing of the pressure residues for the production of insulating material or litter, a less compressing way of pressing can be chosen. Here, a press roll is preferred. In either case, it is preferred that the press residue after pressing contains a moisture content less than 15% (w/w), preferably less than 10% (w/w), and most preferably less than 5% (w/w).

According to an aspect of the invention, the hemp plant is harvested before the seed ripening. The harvest of the hemp plant before seed ripening and the reduced dwelling time of the hemp plant on the field have the advantage that the hemp can be harvested twice a year in Germany or allows for an additional harvest once a year when used as second arable crop.

Preferably, the leafy blossom tops i.e. the uppermost $\frac{1}{5}^{th}$ to $\frac{1}{4}^{th}$ of the *Cannabis* plants are harvested by themselves after 6 to 8 weeks in a "partial harvesting" procedure, while the stems are left on the filed to grow on and produce smaller new leafy blossom tops and longer stems. This yields an increase in the higher protein juice for human or animal consumption and pomace for animal feed which can be used directly, or in silage or dried first. The leftover plant will grow on at a normal rate, as our experiments have shown, producing more leafy blossom tops and longer stems to be harvested at the desired later time. The quality of the fiber demanded on the market determines the harvesting time.

With this method more *Cannabis* juice with high protein content (with all essential amino acids) can be produced. The solid remains (pomace) from the juice extraction from the leafy blossom tops are valuable animal feed and do not compete with the fiber production for industry or the use of the juice for human consumption/application. The pomace can be used as animal feed fresh, dried or in silage. This is valuable contribution to the solution of feeding livestock for a growing world population, not competing with food for humans.

In this way the harvest can be spaced out over time (flexible harvesting), yielding different quality fibers and more fresh *Cannabis* juice and pomace, increasing flexibility to react to market prices. The harvesting time i.e. the height of the stems determines the quality of the fiber: the longer, the thicker, the less flexible, the stronger. Thus the intended industrial use of the fiber may determine the time of the harvest.

At any time of harvest the *Cannabis* plant will produce added value for the farmer from the juices pressed in a quality fit for human consumption and products for application on humans and animals and the catching of evaporating liquids in the hours after harvesting to produce scents or leather treatments, etc.

At seed ripening time *Cannabis Sativa* has grown to typically 250-350 cm. *Cannabis Sativa* has the potential to be the largest biomass producer per season in the plant kingdom. Its tap roots loosen the soil and more importantly, soak up and retain fertilizer not used by preceding crops, thereby preventing superfluous fertilizer to seep into ground water.

Preserving clean drinking water for human consumption is one of the important problems to be solved for the world's future population. It has been established elsewhere that the best quality fiber a *Cannabis Sativa* plant can produce are found in the middle parts of the plant. The lowest $\frac{1}{5}$ and the uppermost $\frac{1}{5}$ are least suitable for fiber production. Therefore roots and bottom $\frac{1}{5}$ parts of the stems may stay on the field until the next crop is ready for planting. Then these plant parts can be hackled and plowed under for better soil quality.

Alternatively the roots can be harvested and hackled and dried and used as fertilizer on other fields. This may be useful, when very high nitrate and nitrite and phosphorous levels are present in the plant.

*Cannabis Sativa* serves the environment by reducing the need for artificial fertilizer. *Cannabis Sativa* therefore is ideal as additional crop, sharing the field with other crops in the same growing season (multiple harvesting). With the proposed procedures the field time is reduced because retting is not necessary. *Cannabis Sativa* can be planted before or after other crops, very early or later in the growing season or planted for better soil quality as go between in rotational farming or planted as pilot crop. It can make use of otherwise unused farmland.

While in all ancient cultures extraction of ingredients from the plant with sugar or alcohol or distillation for human consumption has been used, these extraction processes left the fibers soiled and therefore were in rivalry with the goal to produce quality fibers.

To gain the fibers from the plant stems traditionally the harvested hemp lay for weeks in the rain and sun on the field (called retting process) until it was dry. Then in a process called decortication the fiber was separated from the wood shives. Even though modern harvesting, retting and decortication methods have been developed and the dwelling time of hemp on the filed has been reduced, the juice of the plant is still lost for human consumption and application, despite of its nutritional and medicinal benefits. The presented invention changes this to a congruent relationship of the production for the human and animal benefit with the demands for industry.

Without the loss of bulk (compared to harvest with retting) juice is produced off the separate parts of the plant that was formerly lost. By cutting off the leafy blossom tops and making juice from them, animal feed results from the pomace that industry will not use, while the other parts (fibers and wood shives) can be used by industry as before.

According to an aspect of the invention, the hemp plant is pressed immediately after harvest, without the plant being dried or roasted prior to juice extraction. Without drying or retting, the hemp is pressed as described above to a moisture content of preferably less than 15% (w/w) and thus immediately suitable for storage. The quality of the juice, the leaves as well as of the fibres and shives is not impeded by a direct further processing. Elasticity of the fibres in the stem coat as well as the cellulose fibres in the shives is increased advantageously, which renders them useful for the further application, for example in the production of insulating material and sealing material. Additionally, when employing the methods of the invention, the shives retain their natural light colour so that the further processing to paper or diapers/feminine hygiene products etc. can be carried out with little or no bleaching, which is harmful to the environment and necessary for the production of cellulose material from wood.

The processing of the *Cannabis* plant in a green state after harvesting not only has the advantage of yielding the juice that is lost in the retting process, but also yields a better quality fiber as well as a whiter grade wood shives for the production of all those materials. Therefore the environmental hazards from bleaching chemicals are reduced. Decorticating the stems when they are fresh gives cleaner results, because of the thin layer of plant sap separating the fibers in the outer layer from the inner wood shine structure. Retting dries up this separating layer and wood shives will cling to the fibers.

Another advantage of extracting the juice without prior drying or retting of the plant is the easier and cleaner separation of the fibres from the shives, as those two components are demarcated against each other in the freshly harvested state by a disjunctive layer of plant fluid. This disjunctive plant fluid is lost when traditional methods of drying and retting are applied and shives parts can stick the fibres during chipping and vice versa. This makes further processing steps necessary that can be avoided with the methods of the present invention.

In cases where the plant cannot be further processed immediately, it is stored in closed containers, in which the evaporated fluid is collected. It can later be added to the juice or preferably be used in the processing of leather surfaces or in the production of skin cosmetics, as the evaporated fluid contains substances that smooth leather and/or skin.

Our research has demonstrated that extraction of the *Cannabis* juice with alcohol or with sugar will not yield the full nutritional and medicinal value that the pressed juice according to the present invention provides. To preserve the juice it can be frozen at or below minus 18° C. In the beverages and products proposed the juice is not over-heated so the protein, minerals and vitamins are kept intact. Accordingly as an aspect of the present invention, the hemp plant or the hem plant parts, respectively, are preferably pressed at ambient temperatures, i.e. between 10° C. and 40° C., preferably between 15° C. and 25° C.

To press the separate parts of the *Cannabis* plant separately yields different types of juices. The juice from the leafs plus the leafy blossom tops is dark green and has the most bitter taste. It has the highest protein (including all 8 essential proteins) and carbon content, is highest in Calcium, has the highest content in fatty acids, in polyphenols, nitrate and sulfate. The juice from the fibers is a lighter color green and tastes less bitter, more grass like. It contains essential proteins, contains more minerals and essential minerals than the leafy blossom tops, copper and iron (not found in the leafy blossom tops) and has the highest nitrite and chloride content. The juice from the wood shives is light in color, has a sweetish taste, contains about the same concentration in minerals and essential minerals as the fibers. It is highest in iron.

Out of these cold-pressed *Cannabis* juices (i.e. juice from the entire plant, and/or juice from the leafs plus leafy blossom tops, and/or juice from the fibers, and/or juice from the wood shives, and/or mixtures thereof) diverse beverages and products for human consumption or human application can be produced.

The cold-pressed juice is used as it is or alternatively is fine-filtered in a first step.

The juice obtained by the methods of the present invention is suitable for direct consumption, or it can be carbonated or be fermented to beer like beverage and/or it can be distilled. It can further be used as additive in cosmetics, detergents or preferably after conversion to creams or gels, for medicinal use, like wound healing or healing of skin eczema or for internal application as medicine or for cosmetic usage. Mixed beverages can also be produced from the hemp juice. Preferably, a beer like beverage is brewed from the hemp juice.

Diverse beverages can be produced: without alcohol (soft drinks), mixed with fruit juices, vegetable juices, herbs, spices and/or other ingredients, carbonated and/or uncarbonated; *Cannabis* syrup (*Cannabis* juice mixed with sugar/fructose); beverages with alcohol such as *Cannabis* beer, *Cannabis* wine, *Cannabis* liqueur, *Cannabis* brandy).

The dried remains from the fine filtering and/or the dried *Cannabis* juice can alternatively be used as nutritional supplement and as a taste enhancer (*Cannabis* acts as a taste enhancer for all salty foods) for instance mixed with table-salt, mixed with liquid herbs and spices, mixed with food oils, added to instant soups and sauces as well as ready-made meals, etc. The dried remains and/or the dried juice can be used as food supplement in the form of pressed tablets.

The juice obtained by the methods of the invention is preferably used in the production of beverages. The present invention therefore provides in a further aspect a method for producing beverages on the basis of the hemp plant juice, wherein the hemp juice is mixed with yeast and fermented.

Preferably, the juice of the hemp plant is initially heated to a temperature of over 30° C., preferably over 45° C. Depending on the intended final taste of the beverage, malt extract obtained from different grain can be added to the heated hemp juice. For example, the hemp juice can be mixed with the extract of malted wheat and/or malted rice. Preferably, the hemp juice or mixtures thereof obtained according to b) or c) are mixed with the extract of malted wheat and/or malted rice. The result is a pale, light hemp beverage.

Additionally or alternatively, the hemp juice can be mixed with the extract of malted rye and/or malted barley. Preferably, the hemp juice or a mixture thereof obtained according to a) or b) is mixed with the extract of malted rye and/or malted barley. The result is a strong, dark hemp beverage.

The hemp juice itself or the mixture of hemp juice and extract of malt is preferably brought to boil.

Depending on the intended final taste of the hemp brewage, additional aromatic hop can be heated in the boiling fluid. This is not necessary for creating a bitter taste, as hemp itself is the next relative of hop and has in itself a similar aroma. Thus, further processing is preferably carried out without addition of aromatic hop.

After boiling of the hemp juice or the mixture of hemp juice and malt extract and optionally further ingredients, as described above, the mixture is cooled. You get a "hemp condiment".

The "hemp condiment" is preferably filtered and transferred to a fermenter. The strength of the "hemp beverage" can be changed by addition of water. It is well known that the water quality influences the taste of the beverage. Fruit juice may be added to the "hemp condiment" in the fermenter or at a later stage.

When the "hemp condiment" or a mixture of the "hemp condiment" and fruit juices has been cooled to about 25° C., yeast is added. The choice of yeast, preferably fresh and active brewing yeast, determines the top fermentation or bottom fermentation of the "hemp beverage", respectively, as well as other factors of the beverage's quality. Preferably, the yeast is added by swirling with oxygen.

Juice from the leafy upper third of the hemp stem or hop or further addition of various aromas or various fruit juices can now be added and fermented for the enrichment of taste. The sugar present in the fermenter will ferment to alcohol and carbon. A "hemp mash" is obtained.

If the content of carbon or the content of alcohol after fermentation is not congruent with the intended goal, fermentation is further pushed/propelled under pressure by adding malt sugar or fruit sugar and if applicable additional yeast. During secondary fermentation, temperature is adjusted to the temperature during the main fermentation. The secondary fermentation is the time span of the ripening and will depend on the used yeast and the intended final taste of the beverage.

A refinement of the beverage is preferably achieved by a further ripening period at temperatures between 0° C. and 10° C., preferably 2° C. to 5° C.

The beverage obtained that way is unfiltered or filtered suitable for immediate consumption. It is a beer like "hemp brew" or "hemp brew mixed beverage" with the desired alcohol content as well as the desired content of carbon.

The so obtained beverage, preferably the "hemp mash" formed after primary fermentation can likewise be further processed. For example, it can be distilled for the production of a beverage with higher alcohol content. Methods for the manufacturing of a beverage with higher alcohol content by distillation are well known in the art. The distillation process can e.g. be repeatedly applied. Depending on the intended final taste, herbal essences and/or fruit juices and/or fruit mash (e.g. apple mash, strawberry mash, pear mash, mirabelle mash, plum mash, cherry mash and/or kaki mash) can be added prior to the two last distillation processes.

Preferably, the "hemp mash" is distilled twice without additives. Each middle course of the last distillate is bottled for consumption after storage.

The alcohol content of the distilled beverage should be between 35 Vol. % and 45 Vol. %.

With "liquor", the content of alcohol should be between 15 Vol. % and 55 Vol. % and the sugar content should ne at least 100 g per liter beverage. Natural and natural like aromatic substances may be added allowing for a great variety of tastes.

For the manufacturing of hemp bitter liquor, the first distillation of the above described beverage is preferably further processed. Preferably, the first alcoholic distillate of a suitable "hemp mash" is initially mixed with the corresponding amount of sugar and distilled anew. An amount of herbs and aromas corresponding to the intended final taste may be added prior to the final distillation. The middle course of the last distillate is sweetened and thus turned to liquor.

Preferably, the pure hemp juice distillate is mixed with sugar and with a renewed addition of fresh hemp mash from the upper third of the stem. This mixture is again distilled. The middle course of the last distillate is sweetened in that the amount defined for liquor is added.

EXAMPLE

The *Cannabis Sativa* plant is cut on the field at a length of $1/5^{th}$ to $1/4^{th}$ of the plants height from the ground in a way that the harvested plant does not come in contact with the ground. The plants are placed full length on grids spaced to make room for about 30 cm thick layers and moved to a covered container. In the case of "partial harvesting" the uppermost $1/5^{th}$ to $1/4^{th}$ of the plant i.e. the leafy blossom tops are harvested only and the same procedure is applied of placing them on the grids in a covered container. The container cover is shaped and equipped to collect the evaporated liquids from the plants. This takes place within the first 24 hours after cutting. The containers can be connected to a suction hose siphoning off the air containing the evaporation liquid. This process helps to utilize and space out the time for further processing of the *Cannabis* stems after harvesting.

The resulting liquid can be used as it is for treating leather surfaces to clean and soften them with long lasting results. The liquid can also be used for extracting scents/aroma.

The harvested plant is then pressed a twin-screw extruder to force the juice out of the entire plant. Alternatively, the juices are separately pressed out of the leafs and the leafy blossom tops, out of the fibers, and of the wood shines, respectively, and the resulting juices pressed out of the separate plant parts are mixed in a controlled way.

Before pressing, the cut plant stems may need to be cleaned from soil particles. This can be achieved by air jet.

The resulting solid remains after pressing can be used directly for livestock feed, except for horses. They can be also be dried or stored and fermented in silage. They can also be used to produce lactic acid for the chemical industry. Both products, however, juice and pomace, are valuable as nutrients, medicine and cosmetics for human consumption/application for instance in nutritional supplements. The pomace can be mixed with water and cold-pressed a second time to increase the juices gained from the pressing processes, especially when the pomace used for second pressing still contained a high percentage of humidity after the first pressing. Pomace from second pressing also can be used as animal feed and/or as high fiber nutritional supplements for humans or for technical uses in industry.

The stripped stems are then cut into length required by industry for length of fibers and afterwards decorticated in their fresh green state. The length of fibers vary from less than 0.5 cm for bioplastics, to cellulose for paper of around 4 cm, to textiles with varying length up to 30 cm, to fleece liners with fibers longer than 30 cm.

Alternatively the stems are first decorticated and then cut into the required length. Procedures for decortication of fresh *Cannabis* have been published.

The juices from fibers and wood shives can be mixed in a controlled way and/or mixed with the juices from the leafy blossom tops for the beverages and products for human consumption/application.

The pomace of dried wood shives and the pomace of dried fibers can be used for many diverse products. Wood shives and/or the fibers can be used for printing paper or waterproof packaging or paper for laminated floor boards or teabag paper or cellulose for nappies and hospital diapers or building material or insulating material or filling material or bio-plastics or car interiors or textiles for many uses, or fleece etc. The pressure while extracting the juice has to be very high to dry the solid remains down to 15% (w/w), preferably under 10% (w/w). A hydraulic press or a twin-extruder press may achieve this pressure. If the solid remains are either put in silage for animal feed or for the production of lactic acid, or alternatively used in biogas production, the pomace may still remain humid and contain up to 40% to 50% (w/w). Barrel-roller presses, hydro presses or wine presses can be used.

Alternatively the stripped stems are not decorticated but cut into length of about 4 to 10 cm and then cold-pressed/pressed in the above mentioned hydro press and/or wine press and/or barrel-roller press. A mixed juice is obtained and as solid remains a humid pomace results from these presses containing 40% to 50% (w/w). The humid pomace can be placed in a wet-fermentation biogas plant with water added to produce biogas. Next to the stirring device keeping the liquid in constant motion, rotating grid-paddles collect the fibers from the liquid after the stirring of the liquid and the active bacteria have isolated them. The fibers need to be washed. This process yields in addition to the juice more resulting products: bio-gas, fibers and filling material from the wood shines.

The barrel-roller press is similar to those used as sugar cane presses, they consist of 3 to 7 barrel-rollers in sequence, they have a smooth and/or a serrated surface. The barrel-roller press can be filled continuously. The hydro press consists of a cylinder with holes to act as sieve; in the center of the cylinder on a vertical axis a rubber bulb can be expanded with water to cold-press the juice from the *Cannabis* plant parts. This kind of press exerts the lowest pressure but leaves the fibers intact as far as possible. The hydro press needs to be filled and cleaned alternately. The cylindrical hydraulic press consists of a closed steel cylinder with an outlet valve for the juice at the bottom and a hydraulic piston. It can exert the highest pressure and needs to be filled and cleaned alternately. The twin-screw extruder press has two counter-rotating screws that cut the plant in lengths depending on the serrated pattern cut into the screws. The counter-rotating screws grab the plant parts fed into them in a 90 degree angle and the screws winding build up a pressure against the sheathing which is constructed as a stainless steel fine strainer so the juice is pressed out. This press can be fed continuously. All presses suitable for *Cannabis* have to be very sturdy industrial type presses to be able to cut and press the extremely durable *Cannabis* fibers.

The obtained *Cannabis* juice of the entire plant, or the pure juices from the leafs plus leafy blossom tops separately from the fibers separately from the wood shines and/or controlled mixtures of those juices can be made into beverages and products for human consumption and other products for use on humans in a cosmetic and medicinal way. The remains left in the filter after the juice is filtered are dried and/or powdered and can be used as nutritional supplement, adding Umami and enhancing taste in a mixture with table salt, and/or mixed with dried herbs and spices to be used in a spice shaker, and/or mixed in with liquid spices. The dried *Cannabis* powder can added to ready-made soups, sauces and/or ready-made dishes. It enhances the taste of tomato juice and other vegetable juices. It can be used as bitter herbal tea and/or in tea mixes. We have varied the amount of powder added so that neither the bitter taste nor the *Cannabis* taste is overpowering.

The dried powder can be pressed into tablets to be taken as supplementary nutrition.

The pressed and filtered juices as they are need to be kept frozen to be preserved. Pasteurization may be used at low temperatures.

The undiluted juice has a very bitter taste and may be defrosted and used spoon-wise for self medication. We have used the undiluted juice in tea or on the skin directly; used it in bath water, mixed into self-made skin creams, lotions and soaps. All of those without preservatives so they needed to be kept cool and used up quickly.

The cold-pressed and filtered *Cannabis* juices can be mixed to become soft drinks with fruit juices, vegetable juices and/or with water, sugar and herbs and/or caffeine-containing ingredients, carbonated or un-carbonated. The *Cannabis* juices can also be mixed to brand-name soft drinks.

To these soft-drinks distilled alcohol can be added to make "alcopops" (for instance distilled from the cold-pressed *Cannabis* juice and/or brand-name distilled alcohol). To these soft-drinks beer can be added to make beer-soft drink mixes (for instance mixed with beer brewed from *Cannabis* juice or brewed with *Cannabis* juice and/or mixed with brand-name beers).

*Cannabis* cold-pressed juices can be made durable by adding sugar (glucose and/or fructose) to obtain *Cannabis* syrup. Ascorbic acid may be added to stabilize the color.

The *Cannabis* cold-pressed juice can be the basis for a pure *Cannabis* beer. This is a beverage made from cold-pressed *Cannabis* juice by adding brewer's yeast and then let the mixture ferment. Depending on the alcohol content and/or carbonation desired, sugar may be added to the juice before or after first fermentation. Water may be added to the juice before fermentation as well. To all *Cannabis* beers sugar or fruit juices with a high natural sugar content can be added before final fermentation. For instance a *Cannabis*-Apple-Beer, or a *Cannabis*-Kaki Persimmon-Beer can be produced with good results.

A conventional light colored beer on the basis of barley malt or rice malt or wheat malt or oat malt can be brewed in the known ways, however the hops and/or hop aroma can be replaced in part or entirely replaced by the desired mixture of cold-pressed *Cannabis* juices to obtain a light colored beer. A conventional dark colored beer on the basis of rye malt and/or dark malts from the before mentioned grains can be brewed in the known ways, again the hops and/or hop aroma is replaced by the desired mixture of cold-pressed *Cannabis* juices to obtain for instance a dark colored, stronger beer with a more pronounced bitter taste. The *Cannabis* juice can best be chosen from the leafy blossom tops and added for flavor when the temperature in the brewing process will not rise beyond 60 degrees centigrade any more.

A *Cannabis* wine can be fermented from the cold-pressed *Cannabis* juices alone (for instance selecting a lighter *Cannabis* juice mixture with more juice from the wood shines) by adding wine yeast for fermentation. The alcohol content of the wine is increased adding sugar or fruit juices with a high natural sugar content before fermenting. In these manners a pure *Cannabis* wine or a mixed *Cannabis*-plum or *Cannabis*-apple cider and/or other mixed wines can be produced.

Fermented remains from the fine filtering of the *Cannabis* juices or fermented *Cannabis* juices or fermented *cannabis* beer and/or beer remains or fermented *Cannabis* wine and/or wine remains can be used as basis for distilling alcoholic *Cannabis* beverages with high alcohol content, a "*Cannabis* brandy". The distilling can for instance be repeated and mash from various fruits or herbs can be added such as Apple mash, grape mash, pear mash, Mirabelle mash, Kaki persimmon mash, plum mash and/or cherry mash can be added before fermentation. Preferably to the *Cannabis* distillate is added more *Cannabis* juice and/or *Cannabis* juice extract before further distillation. The Alcohol content of the distilled beverage should be between 35 Vol. % and 45 Vol. %.

In a "Liqueur" the alcohol content should be between 15 Vol. % and 55 Vol. % and the sugar content should be at least 100 gr per liter "Liqueur". Natural aromas and aromas identical to nature may be added as ingredients so that many different tastes of the mixed *Cannabis* Liqueur are possible. This "Liqueur" can be also be made into a *Cannabis* bitter digestif by adding the respective bitter aromas from the *Cannabis* or other herbs before the second distillation and finally adding the sugar. Preferably the pure *Cannabis* juices distillate will be distilled again with the addition of sugar and *Cannabis* juices from the leafy blossom tops. The distillate will be sweetened with the defined amount of sugar for a "Liqueur".

*Cannabis* juices can be made durable by adding 99.8 Vol. % pure alcohol until a mixture containing 15 Vol. % to 55 Vol. % alcohol is achieved. Sugar may be added to this mixture as well.

Even though the best nutritional and medicinal value of the cold-pressed *Cannabis* juice (filtered or unfiltered) is retained by not heating it above 55 degrees centigrade, it may be necessary for the production of beverages and products for human consumption/application to heat the juice above 55 degrees centigrade up to and above 100 degrees centigrade. This can be done. The resulting boiled juice still is superior to any water-extraction from the *Cannabis* plant (i.e. boiling the plant or parts thereof without extracting the juices by cold-pressing the plants).

The invention claimed is:

1. A method for obtaining *cannabis sativa* juice consisting essentially of:
   a) harvesting *cannabis sativa* prior to seed ripeness;
   b) cutting the upper leafy part of the stem of the *cannabis sativa*;
   c) stripping the leaves of the *cannabis sativa* from the remaining stem of the *cannabis sativa*;
   d) separating fibres and shives from each other of the stems of the *cannabis sativa*; and
   e) pressing the leafy part of the stem, the fibres and the shives of the *cannabis sativa* separately under pressure to yield said *cannabis sativa* juice.

2. Method of claim 1, wherein said juice is mixed.

3. Method according to claim 1, wherein said pressing in step (e) of the leafy part of the stem, fibers and shives of the *cannabis sativa* is carried out by use of an extruder.

4. Method according to claim 1, wherein in step b) about ⅓rd to ¼th of the upper leafy part of the stem of the *cannabis sativa* is cut off.

5. Method according to claim 1, wherein no drying or retting of the harvested *cannabis sativa* is carried out.

6. Method according to claim 1, wherein the *cannabis sativa* is harvested between the 6th week and seed ripeness.

7. The method according to claim 1, wherein the pressing is carried out at a pressure of 10 to 300 bar.

8. Method for producing beverages of the *cannabis sativa* juice of claim 1, wherein yeast is added to the *cannabis sativa* juice, and the *cannabis sativa* juice is fermented.

9. Method according to claim 8, wherein the *cannabis sativa* juice is boiled with malt extract from wheat, rice, rye and/or barley prior to the addition of yeast.

10. Method according to claim 8, wherein fruit juice and/or flavours are added prior to fermentation.

11. Method according to claim 8, wherein the *cannabis sativa* juice, which has been fermented is mixed with fruit mash and/or fruit juice and is then distilled.

12. Method according to claim 11, wherein sugar and/or fruit mash is added to the fermented and distilled *cannabis sativa* juice.

13. Method according to claim 12, wherein the fermented, distilled *cannabis sativa* juice, to which sugar and/or fruit mash has been added, is distilled another time and subsequently sweetened.

14. Method of claim 1, wherein said pressing in step e) of the leafy part of the stem, fibers and shives of the *cannabis sativa* is carried out under a pressure of 10 to 300 bar.

15. Method according to claim 1, wherein the pressing is carried out in a twin-screw extruder.

16. Method according to claim 1, wherein the juice is in a beverage, a cosmetic, a cleaning agent, an alcoholic beverage, a cream or a gel.

17. Method of claim 1, wherein said pressing in step e) of the leafy part of the stem, fibers and shives of the *cannabis sativa* is carried out at a pressure of 3 to 200 bar.

* * * * *